United States Patent [19]

Isa et al.

[11] 3,947,507

[45] Mar. 30, 1976

[54] METHOD OF PRODUCING LIQUID OLEFIN POLYMER

[75] Inventors: Hiroshi Isa, Funabashi; Hiroshi Mandai, Chiba; Toshiyuki Ukigai, Yachiyo; Anri Tominaga, Tokyo; Ryozo Taniyasu, Narashino; Masuzo Nagayama, Tokyo, all of Japan

[73] Assignee: Lion Fat & Oil Co., Ltd., Tokyo, Japan

[22] Filed: Feb. 26, 1974

[21] Appl. No.: 446,017

[30] Foreign Application Priority Data

Mar. 5, 1973 Japan.............................. 48-26352
Mar. 5, 1973 Japan.............................. 48-26353

[52] U.S. Cl...... 260/683.15 B; 252/429 C; 252/442; 260/683.15 D; 260/683.9
[51] Int. Cl.²....................... C07C 3/18; C07C 3/21
[58] Field of Search.......... 260/683.15 B, 683.15 D, 260/93.7

[56] References Cited

UNITED STATES PATENTS

| | | | |
|---|---|---|---|
| 3,075,958 | 1/1963 | Kastning et al.................. | 260/93.7 |
| 3,075,960 | 1/1963 | Lovett et al...................... | 260/93.7 |
| 3,113,167 | 12/1963 | Sauer.......................... | 260/683.15 D |
| 3,179,711 | 4/1965 | Antonsen................. | 260/683.15 D |
| 3,261,821 | 7/1966 | Vandenberg.................... | 252/429 C |
| 3,304,295 | 2/1967 | Hagemeyer et al............... | 260/93.7 |

*Primary Examiner*—Paul M. Coughlan, Jr.
*Attorney, Agent, or Firm*—Woodhams, Blanchard and Flynn

[57] ABSTRACT

A method for producing a liquid olefin polymer which comprises polymerizing an α-olefin having 6 – 14 carbon atoms or mixtures thereof, in the presence of a catalyst consisting of an alkali metal hydride, a halide of an element selected from boron and aluminum and a titanium halide, or a catalyst in which metallic lithium or sodium is added to those catalyst ingredients.

20 Claims, No Drawings

METHOD OF PRODUCING LIQUID OLEFIN POLYMER

BACKGROUND OF THE INVENTION

1. Field of the Invention

The present invention relates to a method of producing a liquid olefin polymer, and more particularly, to a method of producing a liquid polymer having a high viscosity index, a high flash point and a low pour point and having a very low viscosity, by polymerizing an α-olefin with the use of a specific catalyst.

2. Description of the prior art

Generally, lubricating oils are roughly classified into petroleum oils, synthetic lubricating oils, fatty oils, etc., but their fields of use are expanding, so that a synthetic lubricating oil is required which has high performance characteristics such as a high flash point, a high viscosity index and a low pour point, and so on. For instance, the lubricating oils used for jet aircraft are desired to have said high performance characteristics under both conditions of extremely low temperatures and higher temperatures.

In automatic speed change gears, high temperature hydraulic machines and other fields, lubricating oils having high performance characteristics are similarly needed. However, petroleum lubricating oils used most widely do not have the combination of properties desired for those specific applications. Attention is being focused on olefin polymer oils from the class of synthetic lubricating oils. The olefin polymer oils are produced by polymerizing olefins, and as the polymerization methods, cationic polymerization using Lewis acids such as aluminum chloride and the like, radical polymerization using heat or peroxides are generally enumerated, but the polymer oils having the desired high viscosity index have not yet been obtained because the polymerization is accompanied by the isomerization reaction of the olefins.

Hence, recently the use of the so-called coordinated anionic Ziegler catalyst that regularly effects the polymerization has become spotlighted, for instance, $C_8$ – $C_{10}$ α-olefins are polymerized with the use of a complex prepared from monoethyl aluminum dichloride and titanium tetrachloride as a catalyst to obtain a liquid polymer having high performance characteristics, namely, a viscosity index above 130. a flash point above 210°C and a pour point below −50°C.

However, the olefin polymer oils (lubricating oils) produced with the use of the usual Ziegler catalyst as it is, cannot satisfy the requirements, for instance, for working oils for aircraft as specified in MIL-H83282 or lubricating oils for jet aircrafts as specified in MIL-H7808 in (U.S. Army Standard). Consequently, in order to pass said standards, said olefin polymer oils are fractionally distilled by molecular distillation. But the distillate satisfying those requirements comprises only 30 – 40% of the starting polymer oils, and therefore, it cannot be said that the method is effective when 60 – 70% of the starting polymer oils is not used effectively.

On the other hand, the nature of the liquid olefin polymers of low viscosity grades is similar to that of squalane which is used in cosmetic compositions. It is desired to replace squalane with liquid olefin polymers because of the unstable supply of the raw material for preparing squalane.

SUMMARY OF THE INVENTION

An object of the present invention is to provide a method of producing a liquid olefin polymer which can be used as a lubricating oil and which is extremely excellent in various kinds of properties so that it can pass even said U.S. ARMY Standards. Another object of the present invention is to provide a method of producing a liquid olefin polymer in a high yield and wherein the liquid olefin polymer has satisfactory properties for use as a lubricating oil and is usable as a replacement for squalane.

The method of producing the liquid olefin polymer in the present invention is characterized by polymerizing α-olefins having 6 – 14 carbon atoms in the presence of a ternary catalyst consisting of (a) an alkali metal hydride, (b) a halide of an element selected from boron and aluminum and (c) a titanium halide, or a quaternary catalyst in which (d) metallic lithium or sodium is added to said ingredients (a), (b) and (c). In said catalysts, as ingredients (a), concretely LiH, NaH, KH, $NaBH_4$, $NaBH(OCH_3)_3$, $LiGaH_4$, $LiAl(C_2H_5)_2H_2$, $NaAl(C_2H_5)_2ClH$, $NaAl(C_2H_5)Cl_2H$, $LiZnH_3$, $NaZnH_3$, $LiBeH_3$, $NaBe(C_2H_5)_2H$, $LiAlH_4$, and the like are enumerated, and particularly, NaH and LiH are preferable from the viewpoints of economy and activity. As ingredient (b), $BCl_3$, $AlCl_3$, $AlBr_3$, $Al(C_2H_5)Cl_2$, and the like enumerated and $AlCl_3$ is preferred. As ingredient (c), $TiCl_4$, $TiF_4$, $TiBr_4$, $TiCl_3H$, and the like are enumerated, and $TiCl_4$ is preferred. Also as ingredient (d), metallic lithium or sodium is enumerated, but metallic sodium has an outstanding effect in lowering the viscosity of the liquid olefin polymer produced.

As described in the foregoing, the catalysts used in the method of the present invention are comprised of said catalyst ingredients (a), (b) and (c) or said ingredients (a), (b), (c) and (d). The ratio of ingredient (a)/ingredient (b) is slightly different depending on the kinds of alkali metal hydrides selected, but it is proper to use the ratio of 0.5 - 6.0 mol of ingredient (a) per mole of ingredient (b). Particularly, in case lithium hydride is used as the ingredient (a), (a) 2.0 – 3.5 mol of the ingredient (a) is used per 1 mol of the ingredient (b), and also, in case sodium or potassium hydride is used as the ingredient (a), it is most preferable to use 0.5 – 5.0 mol of the ingredient (a) per mol of the ingredient (b). The ratio of the ingredient (c) to the ingredient (b) is not particularly limited, but the use of 0.5 – 2.0 mol of the ingredient (b) is preferable per mol of the ingredient (c). The amount of metallic ingredient (d) does not depend on the other ingredients (a), (b) and (c), and the use of more than 0.1 mol % of the ingredient (d) is preferable, but the use of 0.5 – 2.0 mol % thereof is optimum since the use of more than 5 mol % does not produce an effect. The amount of the ingredient (c) based on starting olefins is preferred to be more than 0.2 mol % and accordingly the preferable amount is 1.5 - 3.5 mol % since the use of more than 5 mol % is not so effective.

In the present invention, olefins are polymerized in the presence of a catalyst consisting of said ingredients (a), (b) and (c), or a catalyst consisting of said ingredients (a), (b), (c) and (d). As the starting material olefins, α-olefins having 6 – 14 carbon atoms, preferably, straight chain α-olefins having 6 – 14 carbon atoms are selected, and as particularly preferable examples, hexene-1, octene-1, tridecene-1 and mixtures thereof are enumerated. In order to obtain more excellent high grade lubricating oils, it is preferable to use octene-1, decene-1 or mixtures thereof. In working the method of the present invention in practice, firstly, boron halides, aluminum halides or two or more kinds of those compounds are dissolved in solvents such as diethyl ether, tetrahydrofuran, 1,4-dioxane, and the like, or they are dispersed in proper solvents such as saturated hydrocarbons, and the like. Secondly, one or more kinds of alkali metal hydrides and metallic sodium or lithium are added thereto, as it is or the solvents are distilled for removal, and thereafter, titanium halides and the starting material olefins are added, and those olefins are polymerized, preferably with stirring. The reaction temperature is preferably above 70°C, but the optimum range of the reaction temperature is 90° – 150°C because of a tendency that the yield of the distillate which can be used as the lubricating oil is decreased because the content of dimers are increases at temperatures above 200°C. Also the polymerization reaction can be carried out either with or without the use of the solvents. As the solvents useable for the reaction, paraffinic hydrocarbons containing n-paraffin, isoparaffin and the like, naphthenic hydrocarbons, hydrocarbon halides or mixtures thereof are enumerated, and these are concretely, n-pentane, isooctane, cyclohexane, dimethylcyclohexane, trichloroethane, trichloroethylene, methylchloroform, tetrafluoroethane, and the like. In case of using the solvents for the reaction, the weight ratio of the solvent to the starting material olefins is proper to be in the range of 1 : 2 to 4 : 1, while in case of not using the solvents for the reaction, it is necessary to take sufficient attention for controlling the heat of reaction, because the olefins themselves function as the reaction mediums but the reaction proceeds rapidly. As means for controlling the heat of reaction, a method of gradually adding the raw material olefins or the catalyst and a method of forcibly cooling by an external heat exchanger, etc. are effective. In order to decompose the catalyst after completing the reaction, an alcohol or alkaline aqueous solution is used, but an amine or ammonia gas is most preferable for use so as not to cause the halogen to remain in the liquid olefin polymer which is the reaction product. The liquid polymer sufficiently possesses properties that make it useable as a lubricating oil and it can be employed as a replacement for squalane, pristane, and the like for use in cosmetic compositions or medical raw materials. But when the liquid polymer as more excellent high grade lubricating oil, unreacted olefins or olefin dimers which are existent in slight amounts are desired to be removed by distillation or extraction because those substances are not preferable for the desired performance. Further in order to improve the thermal statility, the remaining double bonds may be hydrogenated. Hydrogenation is easily carried out by the use of a conventional hydrogenation catalyst. A satisfactory polymer is produced by the use of a ternary catalyst in which metallic lithium or sodium is not present in the catalyst used in the present invention, but a further improved liquid olefin polymer, in which the viscosity is lower and olefin trimers are contained in a considerable selection ratio, is obtained by the use of a catalyst containing metallic lithium or sodium.

As described in the foregoing, the present invention provides a method in which $C_6 - C_{14}$ $\alpha$-olefins are polymerized with the use of a catalyst consisting of specific ingredients, and it produces a liquid olefin polymer having a high viscosity index, a high flash point and a low pour paint, said liquid olefin polymer having a considerably lower viscosity at extremely low temperatures. Therefore, as described in the foregoing, in order to obtain a working oil, for instance, a working oil for aircraft, that is desired to have a low viscosity at extremely low temperatures as specified in said MIL-H83282, the unreacted olefins and olefin dimers may merely be distilled so as to remove same from the liquid olefin polymer obtained by the method of the present invention, and the resulting polymer can satisfy all of the specified values. The catalyst system used in the present invention has the disadvantage that the reaction rate is slower in some degree, but the use thereof can easily be repeated because most of the $\alpha$-olefins remain in that form.

Incidentally, the property compared with the case of using the other catalyst systems is shown in the following.

Generally speaking, to lower the viscosity is lowering the polymerization degree of olefins to the lower molecular weight side, and such catalysts as nickel-alkyl aluminum catalyst, and the like are known. But by merely lowering only the polymerization degree, the yield of effective distillate above the trimer is extremely decreased and increased amounts of by-products such as the unreacted olefins and olefin dimers are produced.

TABLE - 1

|  | $Al(C_2H_5)Cl_2$—$TiCl_4$ catalyst** Raw material octene-1 | $LiH$—$AlCl_3$—$TiCl_4$ catalyst Raw material octene-1 | $LiH$—$AlCl_3$—$TiCl_4$—Na catalyst | |
|---|---|---|---|---|
|  |  |  | Raw material octene-1 | Raw material $C_nC^*_{10}$ mixed solution (1 : 1) |
| Viscosity 210°F(cs) above 3.5 | 6.55 | 4.04 | 3.30 | 4.00 |
| 100°F(cs) above 16.5 | 38.65 | 19.30 | 13.70 | 18.50 |
| −40°F(cs) below 3000 | 3000 | 2703 | 1800 | 2400 |
| Viscosity index above 120 | 127 | 120 | 120 | 130 |
| Flash point (°F) above 400 | 405 | 415 | 409 | 440 |
| Fire point (°F) above 475 | 435 | 475 | 450 | 480 |
| Pour point (°F) below −65 | −55 | −70 | −70 | −70 |

*$C_8$ is octene-1, and $C_{10}$ is decene-1
**Comparative catalyst

Hence, it is necessary to lower the polymerization degree to the lower molecular weight side, and simultaneously to narrow the molecular weight distributions. All of such difficulties can be solved by the method of the present invention, and a distillate above trimer having a viscosity of 13 - 20 centistokes at 100°F can be obtained in an 80% or more than 80% yield. Thus as compared with the prior results in which only about 30 - 40% of the trito pentamer useable as the working oil for aircraft could be obtained with the use of conventional Ziegler catalyst, a considerable amount of 70 - 80% thereof can be obtained with the use of the specific catalyst units in the present invention.

DESCRIPTION OF THE PREFERRED EMBODIMENTS

Next, examples and reference examples will be described. All the unit of viscosity is centistokes.

REFERENCE EXAMPLE 1

2000 cc of octene-1 was poured into a four neck flask provided with a stirrer, cooler, nitrogen introduction tube and thermometer, and 4.3 g of monoethyl aluminum dichloride and 21 g of titanium tetrachloride were added as catalysts, and the polymerization was carried out. It was stirred for four hours to keep the polymerization temperature at 20° - 40°C.

After completing the reaction, ammonia gas was blown therein and the resulting precipitate was separated by filtration to remove the catalysts. The resulting crude reaction solution was distilled to remove the unreacted octene and octene dimer, and thereafter, was hydrogenated with the use of Raney nickel as a catalyst at a temperature of 150°C and under the condition of 20 Kg/cm$^2$ of hydrogen pressure to obtain an octene oligomer having the properties shown in TABLE 2. The ratio of the trito pentamer in the oligomer was 50%.

REFERENCE EXAMPLE 2

2000 cc of octene-1 was poured into the four neck flask, and 4.0 g of triethyl aluminum and 20 g of titanium tetrachloride and Raney nickel were added, and they were reacted for four hours at 90° - 100°C. After completing the reaction, it was treated according to the process of REFERENCE EXAMPLE 1 to obtain an octene oligomer having the properties shown in TABLE - 2. The ratio of the tri- to pentamer in the oligomer was 60%.

TABLE - 2

|  | Reference Example - 1 | Reference Example - 2 |
|---|---|---|
| Octene conversion (%) | 80.5 | 89 |
| Yield of dimer (%) | 10.0 | 26 |
| Yield of oligomer (%) | 69.5 | 63 |
| Viscosity (210°F) | 6.55 | 5.38 |
| (100°F) | 38.65 | 29.23 |
| (−40°F) | 30,000 | 10,000 |
| Viscosity index | 127 | 131 |
| Flash point (°F) | 405 | 410 |
| Pour point (°F) | −55 | −60 |

EXAMPLES 1 – 3

200 cc of diethyl ether was poured into the four neck flask, and aluminum chloride was added so as to be dissolved therein, and thereafter, lithium hydride was added. Thereafter, most of the diethyl ether was distilled off and 1800 cc of octene-1 and titanium tetrachloride were poured in. The reaction was carried out for four hours at 100°C - 120°C.

After completing the reaction, it was treated according to the process of the REFERENCE EXAMPLE 1 to obtain an octene oligomer having the properties with the following yield shown in Table - 3.

TABLE - 3

|  | Example-1 | Example-2 | Example-3 |
|---|---|---|---|
| Amount of catalyst |  |  |  |
| LiH (g) | 1.9 | 3.1 | 2.1 |
| AlCl$_3$ (g) | 10.2 | 17.0 | 17.0 |
| TiCl$_4$ (g) | 14.4 | 25.0 | 25.0 |
| Olefin conversion (%) | 83.4 | 87.2 | 29.2 |
| Yield of dimer(%) | 9.7 | 5.6 | 2.9 |
| Yield of oligomer (%) | 73.7 | 81.6 | 26.3 |
| Tri- to pentamer in oligomer (%) | 72 | 80 | 92 |
| Viscosity of oligomer |  |  |  |
| 210°F | 5.02 | 4.29 | 3.69 |
| 100°F | 26.18 | 20.79 | 15.90 |
| −40°F | 5200 | 2800 | 1900 |
| Viscosity index | 131 | 125 | 132 |
| Flash point (°F) | 410 | 412 | 406 |
| Pour point (°F) | −70 | −70 | −70 |

EXAMPLES 4 – 7

EXAMPLES 1 – 3 were repeated with the use of sodium hydride instead of lithium hydride. The yield and performance of the resulting oligomer were shown in TABLE - 4.

TABLE - 4

|  | Example - 4 | Example - 5 | Example - 6 | Example - 7 |
|---|---|---|---|---|
| Amount of catalyst |  |  |  |  |
| NaH (g) | 13.5 | 9.0 | 4.5 | 9.6 |
| AlCl$_3$ (g) | 24.8 | 24.8 | 24.8 | 17.6 |
| TiCl$_4$ (g) | 35.4 | 35.4 | 35.4 | 25.1 |
| Olefin conversion (%) | 34.6 | 88.5 | 87.9 | 62.7 |
| Yield of dimer (%) | 6.0 | 8.3 | 6.8 | 13.8 |
| Yield of oligomer (%) | 28.6 | 80.2 | 81.1 | 48.9 |
| Tri- to pentamer in oligomer (%) | 95 | 85 | 85 | 92 |
| Viscosity of oligomer |  |  |  |  |
| 210°F | 2.90 | 4.04 | 4.34 | 3.44 |
| 100°F | 12.09 | 19.30 | 22.28 | 14.87 |
| −40°F | 1500 | 2700 | 3100 | 1800 |

TABLE - 4-continued

|  | Example - 4 | Example - 5 | Example - 6 | Example - 7 |
|---|---|---|---|---|
| Viscosity index | 98 | 120 | 113 | 115 |
| Flash point (°F) | 410 | 415 | 412 | 410 |
| Pour point (°F) | −75 | −75 | −75 | −75 |

EXAMPLE 8

200 cc of octene-1 was poured into the four neck flask, and 15.0 g of monoethyl aluminum dichloride and 3.1 g of lithium hydride were added and it was stirred for two hours at 30°-40°C, and thereafter, 600 cc of octene-1 and 25 g of titanium tetrachloride were added, and it was reacted for four hours at 100°C – 110°C. After completing the reaction, it was treated according to the process of REFERENCE EXAMPLE 1 to obtain an octene oligomer of 80% yield having a viscosity of 22.05 at 100°F. The ratio of the tri- to pentamer in the oligomer was 75%.

EXAMPLE 9

The process of EXAMPLES 1 – 3 was repeated with the use of dodecene-1 instead of octene-1. An dodecene oligomer was obtained with yield of 82%. The ratio of the trimer in the oligomer was 65%. This oligomer could be used as a cosmetic composition substrate which can be used as a replacement for squalane.

EXAMPLE 10

200 cc of diethyl ether was poured into the four neck flask, and 17 g of aluminum chloride was added so as to be dissolved therein. Thereafter 3.1 g of lithium hydride and 2.0 g of metallic sodium were added, and it was stirred for 30 minutes. Most of the diethyl ether was distilled off, and 800 cc of octene-1 and 25 g of titanium tetrachloride were poured in. The reaction was carried out for four hours at 100° – 130°C.

After completing the reaction, according to the process of REFERENCE EXAMPLE 1, distillation and hydrogenation were carried out to obtain an octene oligomer having the properties shown TABLE - 5. The ratio of the trimer in the oligomer was 65%.

EXAMPLE 11

The process of EXAMPLE 10 was repeated with the use of 0.7 g of lithium instead of metallic sodium. The yield and properties of the resulting oligomer are shown in TABLE 5.

The ratio of the trimer in the oligomer was 60%.

EXAMPLE 12

The process of EXAMPLE 10 was repeated, using 0.2 g of metallic sodium.

The yield and properties of the resulting oligomer are shown in TABLE 5.

The ratio of the trimer in the oligomer was 35%.

EXAMPLE 13

The process of EXAMPLE 10 was repeated, using 800 cc of a mixture of octene-1 with decene-1 instead of octene-1.

The yield and properties of the resulting oligomer are shown in TABLE 5.

The ratio of trimer in the oligomer was 66%.

TABLE - 5

|  | Example - 10 | Example - 11 | Example - 12 | Example - 13 |
|---|---|---|---|---|
| Olefin conversion (%) | 68.4 | 75.0 | 80.0 | 67.0 |
| Yield of dimer (%) | 6.1 | 8.5 | 6.5 | 9.0 |
| Yield of oligomer (%) | 62.3 | 66.5 | 73.5 | 58.0 |
| Viscosity 210°F | 3.3 | 3.72 | 3.95 | 4.0 |
| 100°F | 13.70 | 16.76 | 18.50 | 18.50 |
| −40°F | 1800 | 2400 | 2700 | 2400 |
| Viscosity index | 120 | 121 | 122 | 130 |
| Flash point (°F) | 409 | 410 | 415 | 440 |
| Pour point (°F) | −70 | −70 | −70 | −70 |

EXAMPLE 14

200 cc of diethyl ether was poured into the four neck flask, and 24.8 g of aluminum chloride was added so as to be dissolved therein. Thereafter, 9.0 g of sodium hydride and 2.0 g of metallic sodium were added, and it was stirred for 30 minutes, and thereafter, most of the diethyl ether was distilled off, and 800 cc of octene-1 and 25 g of titanium tetrachloride were added. The reaction was carried out for four hours at 100° – 130°C.

Thereafter, after completing the reaction, according to the process of REFERENCE EXAMPLE 1, distillation and hydrogenation were carried out to obtain an octene oligomer having the properties shown in TABLE - 6.

The ratio of the trimer in the oligomer was 65%.

TABLE - 6

| Olefin conversion | 73.00 |
|---|---|
| Yield of dimer (%) | 8.0 |
| Yield of oligomer (%) | 65.0 |
| viscosity of oligomer | |
| 210°F (cs) | 3.36 |
| 100°F (cs) | 14.35 |
| −40°F (cs) | 2200 |
| Viscosity index | 119 |

TABLE - 6-continued

| | |
|---|---|
| Flash point (°F) | 409 |
| Pour point (°F) | −70 |

We claim:
1. The process of preparing a synthetic lubricating oil, which comprises: dissolving in an inert organic solvent or dispersing in a liquid hydrocarbon a halide substance selected from the group consisting of $BCl_3$, $AlCl_3$, $AlBr_3$, $Al(C_2H_5)Cl_2$ and mixtures thereof, adding an alkali metal hydride to the thus-formed solution or dispersion, distilling off solvent from the solution to concentrate said solution, adding to said concentrated solution or to said dispersion $TiCl_4$ and a liquid monomer selected from the group consisting of α-olefins having from 6 to 14 carbon atoms and mixtures thereof, and polymerizing said monomer at a temperature of above 70°C and below 200°C, the polymerization reaction mixture containing from 0.2 to 5.0 mol percent of $TiCl_4$ based on the monomer, from 0.5 to 2.0 mols of said halide substance per mol of $TiCl_4$ and from 0.5 to 6.0 mol of alkali metal hydride per mol of said halide substance;
   and recovering from the polymerization reaction mixture a liquid synthetic lubricating oil consisting essentially of oligomers of said monomer.

2. The process of claim 1 wherein said monomer is selected from the group consisting of octene-1, decene-1 and mixtures thereof.

3. The process of claim 3 wherein said monomer is selected from the group consisting of hexene-1, octene-1, tridecene-1, and mixtures thereof.

4. The process of claim 1 wherein the polymerization temperature is from 90° to 150°C.

5. The process of claim 4 wherein said halide substance consists of $AlCl_3$.

6. The process of claim 6 wherein said alkali metal hydride is selected from the group consisting of LiH and NaH.

7. The process of claim 5 wherein said alkali metal hydride is selected from the group consisting of LiH and NaH and wherein 8. The process of claim 4 wherein said alkali metal hydride is $LiAlH_4$.

9. The process of claim 4 wherein said alkali metal hydride is $NaBH_4$.

10. The process of claim 1 wherein, in said recovering step, the polymerization reaction mixture is first treated to remove unreacted olefin and olefin dimers, and then the remainder of the polymerization reaction mixture is hydrogenated to obtain said synthetic lubricating oil.

11. The process of preparing a synthetic lubricating oil, which comprises: dissolving in an inert organic solvent or dispersing in a liquid hydrocarbon a halide substance selected from the group consisting of $BCl_3$, $AlCl_3$, $AlBr_3$, $Al(C_2H_5)Cl_2$ and mixtures thereof, adding an alkali metal hydride and lithium metal or sodium metal to the thus-formed solution or dispersion, distilling off solvent from the solution to concentrate said solution, adding to said concentrated solution or to said dispersion $TiCl_4$ and a liquid monomer selected from the group consisting of α-olefins having from 6 to 14 carbon atoms and mixtures thereof, and polymerizing said monomer at a temperature of above 70°C and below 200°C, the polymerization reaction mixture containing from 0.2 to 5.0 mol percent of $TiCl_4$ based on the monomer, from 0.1 to 5 mol percent of lithium metal or sodium metal based on the monomer, from 0.5 to 2.0 mols of said halide substance per mol of $TiCl_4$ and from 0.5 to 6.0 mol of alkali metal hydride per mol of said halide substance;
   and recovering from the polymerization reaction mixture a liquid synthetic lubricating oil consisting essentially of oligomers of said monomer.

12. The process of claim 11 wherein said monomer is selected from the group consisting of hexene-1, octene-1, tridecene-1, and mixtures thereof.

13. The process of claim 11 wherein the polymerization temperature is from 90° to 150°C.

14. The process of claim 13 wherein said halide substance consists of $AlCl_3$.

15. The process of claim 13 wherein said alkali metal hydride is selected from the group consisting of LiH and NaH.

16. The process of claim 14 wherein said alkali metal hydride is selected from the group consisting of LiH and NaH and wherein when said alkali metal hydride is LiH, the molar ratio of LiH to $AlCl_3$ is from 2.0 to 3.5, and when said alkali metal hydride is NaH, the molar ratio of NaH to $AlCl_3$ is from 0.5 to 5.0; the molar ratio of $AlCl_3$ to $TiCl_4$ is from 0.5 to 2.0; the amount of $TiCl_4$ is from 1.5 to 3.5 mol percent based on said monomer; and the amount of said lithium metal or sodium metal is from 0.5 to 2.0 mol percent based on said monomer.

17. The process of claim 13 wherein said alkali metal hydride is $LiAlH_4$.

18. The process of claim 13 wherein said alkali metal hydride is $NaBH_4$.

19. The process of claim 11 wherein, in said recovering step, the polymerization reaction mixture is first treated to remove unreacted olefin and olefin dimers, and then the remainder of the polymerization reaction mixture is hydrogenated to obtain said synthetic lubricating oil.

20. The process of claim 11 wherein said monomer is selected from the group consisting of octene-1, decene-1 and mixtures thereof.

* * * * *

UNITED STATES PATENT AND TRADEMARK OFFICE
CERTIFICATE OF CORRECTION

PATENT NO. : 3 947 507
DATED : March 30, 1976
INVENTOR(S) : Hiroshi Isa et al

It is certified that error appears in the above-identified patent and that said Letters Patent are hereby corrected as shown below:

Column 9, line 32; change "Claim 3" to ---Claim 1---.
Column 9, line 39; change "Claim 6" to ---Claim 4---.
Column 9, line 44; complete Claim 7 by adding the following:
---when said alkali metal hydride is LiH, the molar ratio of LiH to $AlCl_3$ is from 2.0 to 3.5, and when said alkali metal hydride is NaH, the molar ratio of NaH to $AlCl_3$ is 0.5 to 5.0; the molar ratio of $AlCl_3$ to $TiCl_4$ is from 0.5 to 2.0; and the amount of $TiCl_4$ is from 1.5 to 3.5 mol percent based on said monomer.---.

Signed and Sealed this twenty-ninth Day of June 1976

[SEAL]

Attest:

RUTH C. MASON
Attesting Officer

C. MARSHALL DANN
Commissioner of Patents and Trademarks